United States Patent [19]

Townsend et al.

[11] 4,123,524

[45] Oct. 31, 1978

[54] SYNTHESIS OF 6-AMINO-4-METHYL-8-(β-D-RIBOFURANOSYL)PYRROLO[4,3,2-DE]-PYRIMIDO[4,5-C]PYRIDAZINE-5'-PHOSPHATE AS A NOVEL COMPOUND AND ITS UTILITY AGAINST L-1210 MOUSE LEUKEMIA

[75] Inventors: Leroy B. Townsend; Arthur F. Lewis; Linda W. Roti Roti, all of Salt Lake City, Utah

[73] Assignee: The United States of America as represented by the Department of Health, Education and Welfare, Washington, D.C.

[21] Appl. No.: 804,601

[22] Filed: Jun. 8, 1977

[51] Int. Cl.$^2$ .................. A61K 31/70; C07H 19/02
[52] U.S. Cl. ................................ 424/180; 536/28; 536/26; 536/27; 536/24; 536/23; 536/29
[58] Field of Search ................ 536/28, 26; 424/180

[56] References Cited

U.S. PATENT DOCUMENTS 3,413,282  11/1968  Yoshikawa et al. ................ 536/28

OTHER PUBLICATIONS

Towsend, L. and Schram, K., Tetrahedron Letter, 1971, No. 49, pp. 4757–4760.

Primary Examiner—Johnnie R. Brown
Assistant Examiner—Blondel Hazel
Attorney, Agent, or Firm—John S. Roberts, Jr.; Norman J. Latker; Thomas G. Ferris

[57]  ABSTRACT

The compound 6-amino-4-methyl-8-(β-D-ribofuranosyl)pyrrolo[4,3,2-de]pyrimido[4,5-c]pyridazines-5'-phosphate (a nucleotide) as a new compound and its method of synthesis by phosphorylation of the known 6-amino-4-methyl-8-(β-D-ribofuranosyl)pyrrolo[4,3,2-de]pyrimido[4,5-c]pyridazine (a nucleoside). The 5'-phosphate ester has utility against L-1210 mouse leukemia and has superior solubility over the parent compound which gives it a broader use pattern relative to dosage. This novel nucleotide also shows advantage in utilization as to pH over, for example, the hydrochloride salt which gives in solution a pH of 4 and is too acid for use.

2 Claims, No Drawings

SYNTHESIS OF 6-AMINO-4-METHYL-8-(β-D-RIBOFURANOSYL)-PYRROLO[4,3,2-DE]PYRIMIDO[4,5-C]PYRIDAZINE-5'-PHOSPHATE AS A NOVEL COMPOUND AND ITS UTILITY AGAINST L-1210 MOUSE LEUKEMIA

The synthesis of the 5'-phosphate or 6-amino-4-methyl-8-(β-D-ribofuranosyl)pyrrolo[4,3,2-de]pyrimido-[4,5-c]pyridazine-5'-phosphate, a nucleotide, from the parent nucleoside compound [Schram and Townsend, *Tetrahedron Letters,* 49:4757–4760 (1971)] is set out below in Formula I:

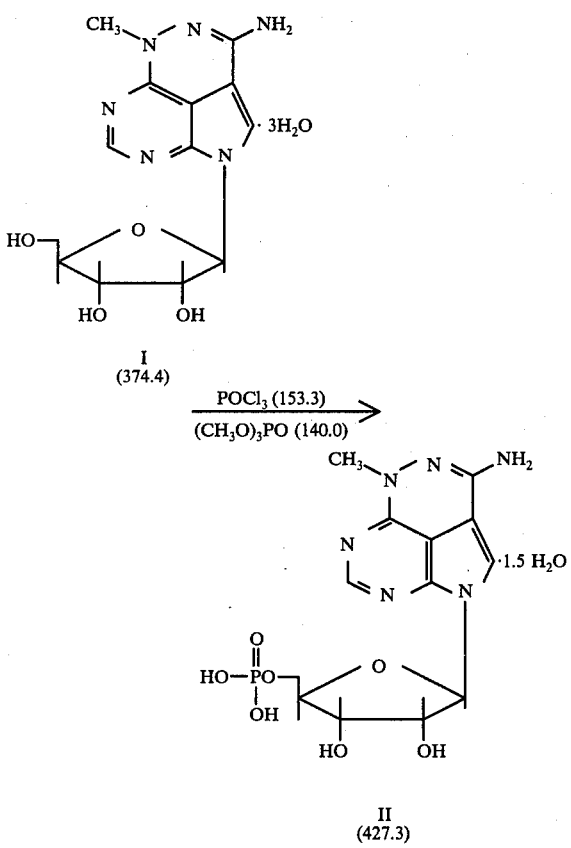

6-Amino-4-methyl-8-(β-D-ribofuranosyl)pyrrolo[4,3,2-de]pyrimido[4,5-c]pyridazine-5'-phosphate (II, NSC #280594) was synthesized by a direct phosphorylation of 6-amino-4-methyl-8-(β-D-ribofuranosyl)pyrrolo[4,3,2-de]pyrimido[4,5-c]pyridazine (I, NSC #154020) by a modification of the procedure of Yoshikawa, et al, *Tetrahedron Letters,* 50:5065 (1967) and using the isolation procedure described for adenosine monophosphate by Imai et al, *J. Org. Chem.,* 34:1547 (1969).

The method utilized the phosphoryl chloride in excess (3–5 molar excess) at 0°–10° C. for 2–4 hours. Trialkyl phosphate was used as an accelerator for the phosphorylation and facilitates the phosphorylation with phosphoryl chloride (or phosphorous oxychloride). Anhydrous trialkyl phosphates, such as trimethyl and triethyl phosphates, are preferred and advantage is taken of the solubility of the nucleoside in the trialkyl phosphate. Typical yields run 20–30%.

PRIOR ART

U.S. Pat. No. 3,502,649 Thiel et al.
U.S. Pat. No. 3,590,029 Koch et al.
U.S. Pat. No. 3,819,613 Marumoto et al.
U.S. Pat. No. 3,936,439 Marumoto et al.

None of the above patented compounds show the novel tricyclic structure of the present compound.

The phosphate ester compound shown above as II has shown activity in a broad range of dosages against L-1210 mouse leukemia.

It has been found that the cytotoxicity for L-1210 in vitro is similar for the 5'-monophosphate (II) and NSC 154020 (I), with $ID_{50}$'s of $2.5 \times 10^{-8}M$ and $3.5 \times 10^{-8}M$ respectively.

The 5'-monophosphate (II) shows anti-L-1210 in vivo comparable to NSC 154020, but over a broader range of dosages and without the host toxicity associated with treatment with NSC 154020.

The modus of treatment is intraperitoneal and the dosage to the host mice is approximately 8–62 mg/kg per diem. A typical course involved daily treatment for 9 days.

The protocol utilized was Protocol 11 of the National Cancer Institute published in Cancer Chemotherapy Reports of September 1972, Volume 3, No. 2, Part 2.

Application of the anticancer tricyclic nucleoside (I above) has been hindered by formulation (insolubility) problems. The present water-soluble 5'-phosphate ester of this nucleoside has apparently solved the insolubility problem.

EXAMPLE 1

The nucleoside (I, 1.6 g, 4.7 mmoles) was dissolved in 30 ml of dry, redistilled trimethyl phosphate. The solution was stirred and cooled to $0° \pm 2°$ C. A mixture of 2 ml (3.35 g, 21.9 mmole) of phosphorous oxychloride and 5 ml of trimethyl phosphate was added slowly (approx. 30 min) maintaining a reaction temperature of $0° \pm 2°$ C. The reaction was stirred in the cold ($0° \pm 2°$ C.) for 30 min. more and then refrigerated ($0° \pm 2°$ C.) for 16 hr. The reaction was poured onto 100 ml of crushed ice and the resulting solution stirred for approx. 15 min. The pH was adjusted to 2 by the addition of cold 4 N sodium hydroxide. The solution was extracted with chloroform (3 × 100 ml) and then stirred with 40 g of activated charcoal. The charcoal was first washed with water (1 l) and then ethanol—conc. ammonium hydroxide—water (25:1:24 v/v/v) approx. 1.5 l) to elute the reaction products. The alcoholic-ammonia solution was evaporated in vacuo to a volume of approx. 50 ml, and this solution then applied to a column of Dowex 1 × 8 ($HCOO^-$) (25 ml). The Dowex was washed with water until no detectable u.v. absorbing material was eluting (750 ml). The Dowex was then washed with 0.05 N formic acid (500 ml) and then with 0.1 N formic acid (2 l), collecting 20 ml fractions. The fractions containing the major product (35–95) were combined and the solution evaporated in vacuo to a volume of 100 ml. Ethanol (100 ml) was added and the mixture refrigerated for several hours. The solid was collected by filtration, washed with ethanol (20 ml) and dried in vacuo. Yield = 390 mg (0.913 mmole, 21%). The solid was recrystallized from water (65% recovery) and dried in vacuo to give a pure compound. Anal. calc'd for $C_{13}H_{17}N_6O_7P \cdot 1.5\ H_2O$: C, 36.54; H, 4.72; N, 19.67; O, 31.83. Found: C, 36.54; H, 4.72; N, 19.88; O, 31.07. U.v. $\lambda_{max}$ (nm), $\epsilon \times 10^{-3}$: pH 1, 315 (5.66), 287

(11.4), 280.5 (11.4); pH 11, 320 sh (7.37), 292 (12.6); methanol, 322 sh (7.37), 293 (12.8). U.v. $\lambda_{min}$, $\epsilon \times 10^{-3}$: pH 1, 258 (5.13), pH 11, 256 (3.11); methanol, 257.5 (2.88).

A 34% yield of the 5'-phosphate (II) was obtained when anhydrous I (4 mmole) was allowed to react with 3 equivalents (12 mmoles) of phosphorous oxychloride which had been prereacted with 1 equivalent (4 mmoles) of water.

EXAMPLE 2

Activity of Tricyclic Nucleoside (NSC #154020) and the 5'-Monophosphate (NSC #280594) Against L-1210 in vivo as Indicated in Survival Times of L-1210 Bearing Mice T/C = Mean Lifespan of Treated Animals/Mean Lifespan of Control Animals

| Molar Equivalent Dose (in water)/Injection) (mg/kg administered intro- peritoneally on Days 1–9) | | T/C (%) | |
|---|---|---|---|
| | | Nucleoside | Nucleotide (5'Phosphate Derivative) |
| NSC #154020 | NSC #280594 | NSC #154020 | NSC #280594 |
| 50 | 62.5 | (toxic) | 143 |
| 37.5 | 46.9 | (toxic) | 174 |
| 25 | 31.25 | (toxic) | 159 |
| 18.75 | 23.45 | 135 | 153 |
| 12.5 | 15.63 | 148 | 125 |
| 9.4 | 11.73 | 126 | 132 |
| 6.25 | 7.81 | 129 | 132 |

As above noted and in extensive additional testing, Compound I, the nucleoside (NSC #154020), has shown consistently good activity against mouse leukemia L-1210 in vivo, in the approximate dose range 6–19 mg/kg, with T/C's ranging up to 215, with two cures (animals surviving 30 days). Host toxicity prevented the use of higher doses. In contrast, the nucleotide (5'-phosphate derivative) NSC #280594 has shown excellent activity with no host toxicity up to 62.5 mg/kg, the highest dose tested.

We claim:

1. The compound 6-amino-4-methyl-8-($\beta$-D-ribofuranosyl)pyrrolo[4,3,2-de]pyrimido[4,5-c]pyridazine-5'-phosphate.

2. The method of alleviating and treating L-1210 mouse leukemia which comprises injecting intraperitoneally over a 9-day administration span daily an antileukemic dosage of the compound 6-amino-4-methyl-8-($\beta$-D-ribofuranosyl)pyrrolo[4,3,2-de]pyrimido[4,5-c]pyridazine-5'-phosphate in a dose range of 8–62 mg/kg.

* * * * *